US012623023B2

(12) United States Patent
Plumptre et al.

(10) Patent No.: US 12,623,023 B2
(45) Date of Patent: May 12, 2026

(54) DRUG DELIVERY DEVICE AND METHOD TO MODIFY A DRUG DELIVERY DEVICE

(71) Applicant: Sanofi, Paris (FR)

(72) Inventors: David Aubrey Plumptre, Warwick (GB); Robert Veasey, Warwick (GB); Paul Griffin, Warwick (GB); Rory James Livingston Hawkins, Warwick (GB); Tom Alexander Earwaker, Warwick (GB)

(73) Assignee: Sanofi, Paris (FR)

( * ) Notice: Subject to any disclaimer, the term of this patent is extended or adjusted under 35 U.S.C. 154(b) by 1149 days.

(21) Appl. No.: 17/260,411

(22) PCT Filed: Jul. 15, 2019

(86) PCT No.: PCT/EP2019/068975
§ 371 (c)(1),
(2) Date: Jan. 14, 2021

(87) PCT Pub. No.: WO2020/016166
PCT Pub. Date: Jan. 23, 2020

(65) Prior Publication Data
US 2021/0260292 A1 Aug. 26, 2021

(30) Foreign Application Priority Data
Jul. 18, 2018 (EP) ..................................... 18305980

(51) Int. Cl.
A61M 5/24 (2006.01)
A61M 5/315 (2006.01)

(52) U.S. Cl.
CPC ............ A61M 5/24 (2013.01); A61M 5/2422 (2013.01); A61M 5/31576 (2013.01); *A61M 2005/2477* (2013.01)

(58) Field of Classification Search
CPC .. A61M 2005/2403; A61M 2005/2407; A61M 2005/2411; A61M 2005/2433;
(Continued)

(56) References Cited

U.S. PATENT DOCUMENTS 5,891,106 A * 4/1999 Butuzov ................. A61M 5/24
604/209
9,132,237 B2 * 9/2015 Harms .............. A61M 5/31585
(Continued)

FOREIGN PATENT DOCUMENTS

CN 102245235 11/2011
CN 102458520 5/2012
(Continued)

OTHER PUBLICATIONS

PCT International Preliminary Report on Patentability in International Application No. PCT/EP2019/068975, dated Jan. 19, 2021, 7 pages.
(Continued)

*Primary Examiner* — Shefali D Patel
(74) *Attorney, Agent, or Firm* — Fish & Richardson P.C.

(57) ABSTRACT

A drug delivery device is proposed, the drug delivery device comprising: a housing; a drive mechanism; a cartridge containing a drug, the cartridge being retained in a defined position relative to the housing, wherein the drive mechanism is configured to dispense the drug from the cartridge; a cartridge bias system, which comprises at least one resilient member and at least one rigid force transfer body, wherein the at least one rigid force transfer body is movably located within the housing, wherein the cartridge bias system is arranged and configured to exert a force on the cartridge to maintain the cartridge in the defined position, wherein the force is provided by the at least one resilient member, and wherein the at least one rigid force transfer (Continued)

body is operatively connected to the at least one resilient member such that the force is reacted by the at least one rigid force transfer body. Further, a method to modify a drug delivery device is disclosed.

16 Claims, 5 Drawing Sheets

(58) Field of Classification Search
CPC .... A61M 2005/2437; A61M 2005/244; A61M 2005/2477; A61M 2005/2481; A61M 2005/2485; A61M 2205/0216; A61M 5/24; A61M 5/2422; A61M 5/315; A61M 5/31565; A61M 5/31576
See application file for complete search history.

(56) References Cited

U.S. PATENT DOCUMENTS

| | | | |
|---|---|---|---|
| 2005/0171476 A1 | 8/2005 | Judson et al. | |
| 2011/0306939 A1* | 12/2011 | Harms | A61M 5/24 |
| | | | 29/446 |
| 2013/0310746 A1 | 11/2013 | Wozencroft | |

FOREIGN PATENT DOCUMENTS

| | | |
|---|---|---|
| CN | 106714877 | 5/2017 |
| EP | 1423079 | 7/2006 |
| EP | 2043708 | 12/2010 |
| JP | H10-511016 | 10/1998 |
| JP | 2012-504992 | 3/2012 |
| JP | 2012-528623 | 11/2012 |
| JP | 2014-521408 | 8/2014 |
| JP | 2017-527404 | 9/2017 |
| KR | 10-2011-0070895 | 6/2011 |
| KR | 10-2017-0026562 | 3/2017 |
| WO | WO 1996/017640 | 6/1996 |
| WO | WO 2010/043533 | 4/2010 |
| WO | WO 2010/139635 | 12/2010 |
| WO | WO 2011/032883 | 3/2011 |
| WO | WO 2012/064258 | 5/2012 |
| WO | WO 2012/130704 | 10/2012 |
| WO | WO 2013/010973 | 1/2013 |
| WO | WO 2016/001299 | 1/2016 |
| WO | WO 2016/042076 | 3/2016 |
| WO | WO 2016/065220 | 4/2016 |
| WO | WO 2016/091554 | 6/2016 |
| WO | WO 2016/150900 | 9/2016 |
| WO | WO 2017/186435 | 11/2017 |

OTHER PUBLICATIONS

PCT International Search Report and Written Opinion in International Application No. PCT/EP2019/068975, dated Oct. 4, 2019, 11 pages.

* cited by examiner

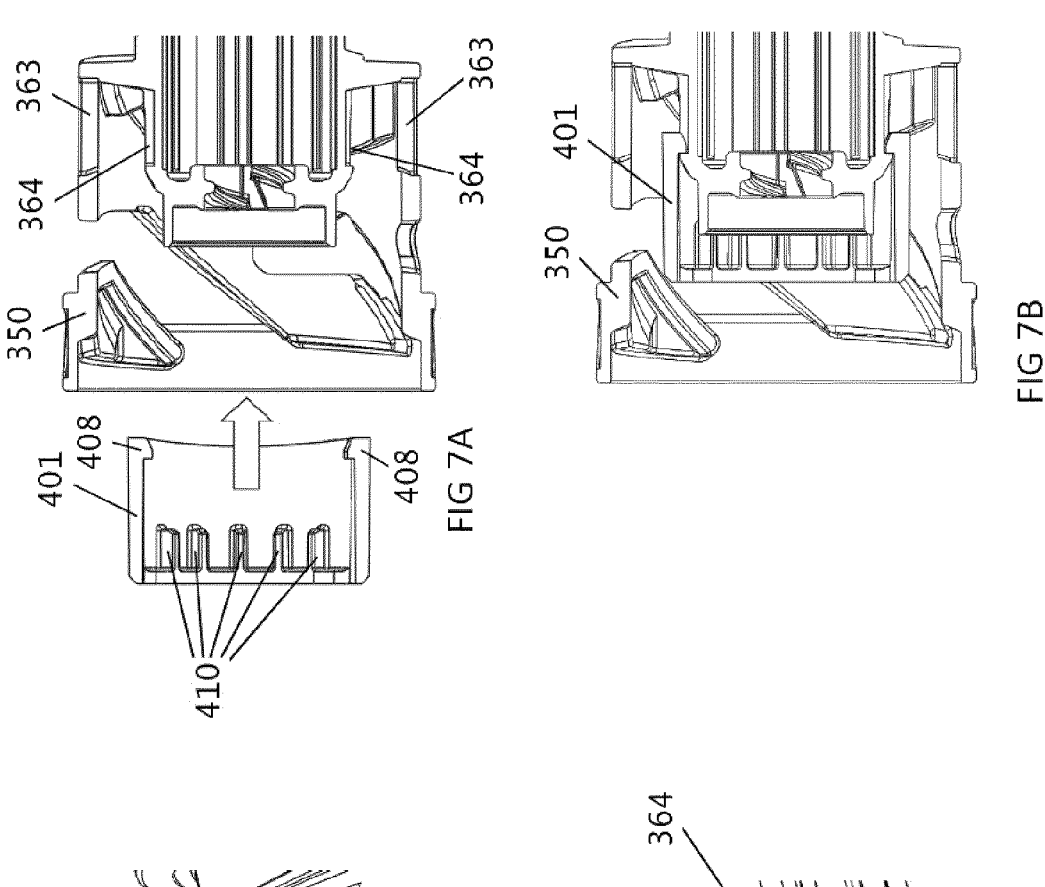
FIG 7A
FIG 7B
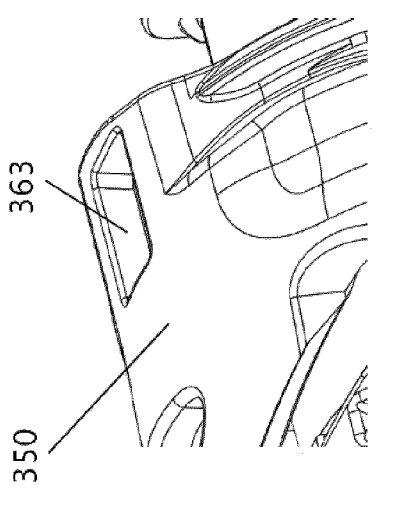
FIG 5
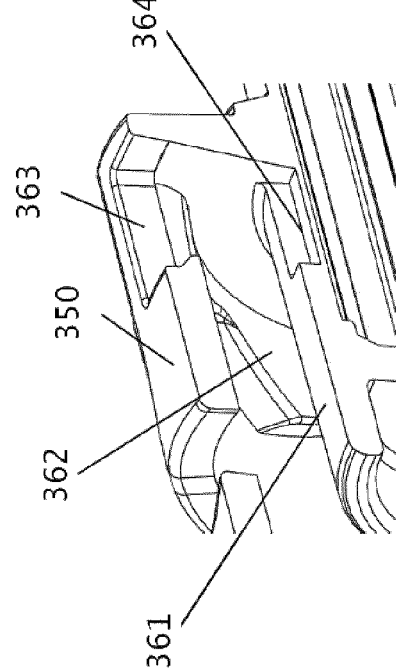
FIG 6

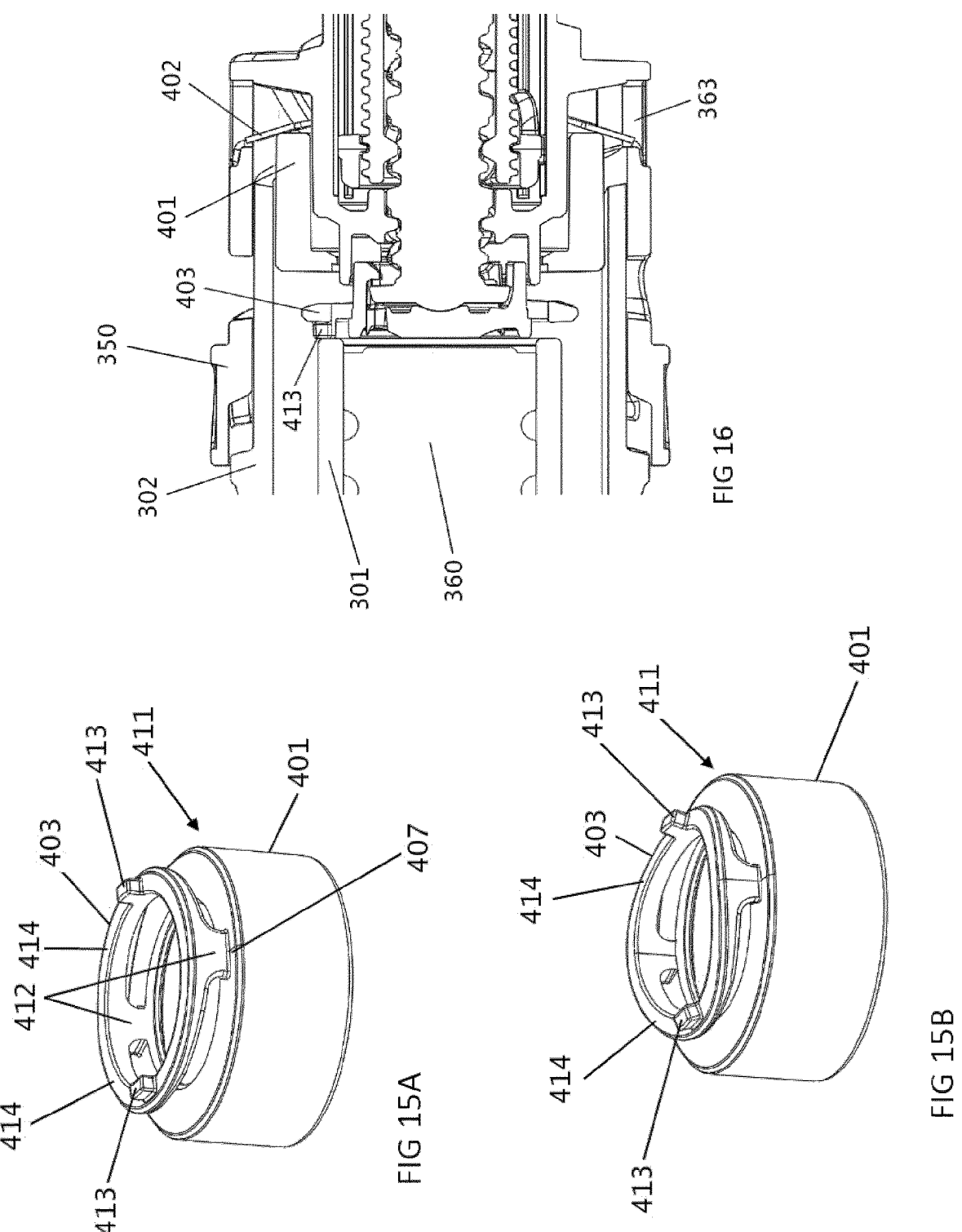

DRUG DELIVERY DEVICE AND METHOD TO MODIFY A DRUG DELIVERY DEVICE

CROSS-REFERENCE TO RELATED APPLICATIONS

The present application is the national stage entry of International Patent Application No. PCT/EP2019/068975, filed on Jul. 15, 2019, and claims priority to Application No. EP 18305980.7, filed on Jul. 18, 2018, the disclosures of which are incorporated herein by reference.

TECHNICAL FIELD

The present disclosure relates to a drug delivery device, in particular to an injection device, such as a pen-type drug delivery device and/or a pen-type injector. Furthermore, the present disclosure relates to an arrangement comprising two drug delivery devices. Also, the disclosure relates to a method of modifying a drug delivery device.

BACKGROUND

Often, in drug delivery devices a cartridge bias member such as a spring is provided which biases the cartridge to maintain the cartridge in a defined position relative to other elements of the device. This may ensure that accurate doses are delivered from the drug delivery device as the cartridge can be immobilized and does not move during setting and/or delivery of a dose. The cartridge bias member may be provided to account for manufacturing tolerances which cause small variations in the length of cartridges within the range of manufacturing tolerances, although the cartridges nominally should have the same lengths.

SUMMARY

Certain aspects provide improvements relating to cartridge bias system or arrangement which are used to bias cartridges in drug delivery devices.

An aspect of the present disclosure relates to a drug delivery device. The drug delivery device comprises a housing. The housing may have a tubular shape, for example. The housing may be a sleeve. The drug delivery device further comprises a drive mechanism. The drive mechanism may be movably retained in the housing. The drive mechanism may comprise a piston rod, for example. The piston rod may be movable in the distal direction relative to the housing to dispense drug. The drug delivery device further comprises a cartridge which contains a drug or medicament, particularly an amount sufficient for a plurality of, preferably user-settable, doses. The cartridge may comprise a bung which may be driven distally with respect to a cartridge body of the cartridge in order to dispense drug or medicament which is retained in the cartridge, such as liquid drug or medicament, from the cartridge. The cartridge is expediently retained in a defined position relative to the housing. The drive mechanism may be configured to dispense drug from the cartridge. For example, distal movement of the piston rod may be transferred to the bung such that the bung is moved relative to the cartridge body in the distal direction. The drug delivery device further comprises a cartridge bias system. The cartridge bias system comprises at least one resilient member, such as only one resilient member or a plurality of resilient members such as two resilient members, and at least one rigid force transfer body, such as only one force transfer body or a plurality of force transfer bodies. The rigid force transfer body is preferably rigid at least against deformations in the axial direction. Accordingly, the rigid force transfer body may be used to transfer axial forces within the drug delivery device. The rigid force transfer body is movably retained in the housing. The force transfer body may be rotationally locked relative to the housing but axially movable relative to the housing. Alternatively, the force transfer body may be rotationally and axially movable relative to the housing. The axial movement of the force transfer body relative to the housing is preferably constrained, for example by a distal stop, which limits distal movement of the force transfer body relative to the housing, and/or a proximal stop, which limits proximal movement of the force transfer body relative to the housing. When the body abuts the respective stop further movement may be prevented in the distal or proximal direction.

The cartridge bias system of the drug delivery device is arranged and configured to exert a force on the cartridge to maintain the cartridge in the defined position. The force is preferably provided by the resilient member. The force may be a distally directed force. The rigid force transfer body may be operatively connected to the resilient member and/or the cartridge such that the force is reacted by the force transfer body and/or transferred to the cartridge via the force transfer body. In other words, the rigid force transfer body may be arranged in the load path between the resilient member and the cartridge. For example, the rigid force transfer body may be arranged between the resilient member and the cartridge. The resilient member may be arranged proximally with respect to the force transfer body. The rigid force transfer body may be arranged proximally with respect to the cartridge. The cartridge bias system may be retained in the housing.

Providing the rigid force transfer body in addition to the resilient member has a variety of advantages. For example, by providing the rigid force transfer body, the resilient member can be tailored to its primary functions, i.e. exerting an elastic restoring force when deformed, which tends to establish the non-deformed shape of the resilient member. The force may be an axially directed force, preferably without an angularly directed component. Particularly, the dimensions of the cartridge need not be accounted for in the design of the resilient member. Thus, the dimensions of the resilient member can be adjusted to the available room in the housing without the need to consider the cartridge dimension. The rigid force transfer body may provide a bridge or spacer which provides operative connection between the resilient member and the cartridge. Further, the rigid force transfer body may be used to adjust an existing drug delivery device for usage with a cartridge of a different dimension such as of a reduced length and/or diameter, for example as will be explained further below. Thus, the rigid force transfer body may provide improvements with respect to the design for the resilient member and/or with respect to the variability of the device which can be used with different cartridges more easily when the rigid force transfer body is added to an existing device. Moreover, as the force transfer body is rigid, there is no need to adjust resilient members in the systems to another axially flexible element in the system. Rather, standard resilient members can be applied which are only adjusted to a cartridge of a new dimension or length by means of the rigid force transfer body.

In an embodiment, the rigid force transfer body has a first load transfer surface which faces the cartridge and a second load transfer surface which faces away from the cartridge. The first load transfer surface may be a distal surface that is to say a surface which faces in the distal direction and the second load transfer surface may be a proximal surface that is to say a surface which faces in the proximal direction.

In an embodiment, the resilient member is a spring washer, e.g. a metal spring washer. Spring washers provide high forces with comparatively low axial deformation.

In an embodiment, the resilient member is arranged on that side of the rigid force transfer body, which faces away from the cartridge. That is to say the resilient member may be arranged on the proximal side of the rigid force transfer body. This resilient member may interact with the second load transfer surface of the force transfer body, preferably abut this surface. The force transfer body may cover the resilient member when the cartridge is detached and/or protect the resilient member from being accessed by the user.

In an embodiment, the resilient member is provided to abut a stop surface of the housing, which prevents relative movement of the resilient member relative to the housing in the proximal direction. Thus, this surface or stop may counteract a force transferred via the rigid force transfer body to the surface via one or more of the resilient members. Consequently, this surface assists in maintaining the cartridge in the defined position.

In an embodiment, the cartridge bias system comprises a plurality of resilient members, e.g. two resilient members or more than two. The respective resilient member may be a spring washer such as a metal spring washer, for example. The plurality of resilient members may be operatively connected in series. By means of a plurality of resilient members, the force transferrable to the cartridge by means of the cartridge bias system and/or the axial deformability of the cartridge bias system may be increased.

In an embodiment, the rigid force transfer body is made of plastic. This facilitates cost-effective manufacturing of the body, e.g. by molding such as injection molding.

In an embodiment, at least one of the resilient members is a metal spring member, e.g. only one of the members or both of the two resilient members are metal spring members. All resilient members may be metal spring members.

In an embodiment, the rigid force transfer body is arranged between and/or in the load path between the two resilient members. Consequently, one resilient member may be arranged proximally relative to the second load transfer surface, preferably in abutment with this surface, and one resilient member may be provided distally relative to the first load transfer surface, preferably in abutment with this surface.

In an embodiment, the rigid force transfer body is arranged in the load path between and/or between the two resilient members and the cartridge. That is to say, two resilient members may be provided proximally relative to the second load transfer surface of the rigid force transfer body. One resilient member may be in abutment with the second load transfer surface and the other resilient member may be in abutment with the one resilient member.

In an embodiment, the rigid force transfer body is arranged distally relative to the resilient member, preferably distally with respect to at least one metal spring member or all resilient members. Preferably, a distal surface of the rigid force transfer body like the first load transfer surface may cover the resilient member(s) arranged proximally relative to this surface axially and angularly.

This arrangement has the advantage that, in case the cartridge is disconnected from the housing, preferably only a distal surface of the rigid force transfer body may be visible and the resilient member(s) may be invisible. Particularly, the rigid force transfer body may prevent that the user can reach one or more resilient members and tamper with these members.

Accordingly, safety is increased. Metal spring member do often have sharp edges which can harm the user, if touched. The force transfer body may prevent that the resilient member(s) can be touched.

In an embodiment, the resilient member, e.g. one of the resilient members such as only one of the resilient members, is formed in a unitary body structure with the rigid force transfer body. The other resilient member is expediently a metal spring member, preferably arranged proximally with respect to the force transfer body. Thus, the unitary body structure may comprise a rigid section for the force transfer body and an elastically deformable section for the resilient member. The elastically deformable section may be arranged at the distal end of the unitary body structure. By forming one of the resilient members unitarily with the rigid force transfer body, which may be of plastic, a plastic surface can be provided at the distal end of the cartridge bias system. Accordingly, sharp metal edges may be avoided at the distal end which is particularly easy to be reached by the user, if the cartridge has been removed.

In an embodiment, the resilient member, e.g. one of the resilient members, is rigidly secured to the rigid force transfer body. In this way, one of the resilient members, e.g. a metal spring member, may be provided at the distal surface but another resilient member is still provided proximally relative to the rigid force transfer body. Therefore, it is possible that only one of a system comprising two resilient members has to be customized for a specific cartridge.

In an embodiment, one of the resilient members, e.g. only one, is rigidly secured to the rigid force transfer body and/or at least one of the resilient members is not rigidly secured to the force transfer body. Rigidly secured may mean in this context, that the resilient member and the force transfer body may be assembled to each other such that they can be handled as one entity. For example, the resilient member may be rotationally and/or axially secured relative to the force transfer body.

In an embodiment, the resilient member, e.g. only one of the resilient members or two of the resilient members or all of the resilient members, has a, preferably central, opening. The inner diameter of the opening may be greater than the outer diameter of the cartridge. Thus, the cartridge may be dimensioned such that it could be guided through the opening. Accordingly, although the dimensions of the resilient member are not suitable for biasing the cartridge, the rigid force transfer body may be used to transfer load or force between the cartridge and the resilient member. A resilient members with a greater diameter may be manufactured more easily to provide high forces, e.g. as more material, such as metal, can be used. If there are a plurality of resilient members, all of the resilient members or only a part of the resilient members may have an opening with the specific dimension. For example, a first one of the resilient members may have an opening with an inner diameter which is greater than the outer diameter of the cartridge and another resilient member, preferably provided distally relative to the first resilient member, may have an inner diameter which is less than or equal to an outer diameter of the cartridge. The latter resilient member with the lower diameter of the opening may be used to mechanically abut the cartridge, e.g. a proximal end or rim of the cartridge body.

In an embodiment, two resilient members have openings of different diameters. One opening may have a diameter greater than the diameter of the cartridge and the other one may have a diameter less than the (outer) diameter of the cartridge.

In an embodiment, the rigid force transfer body comprises one or more body connection features. By way of the body connection features, the rigid force transfer body may be connected to the housing, preferably movably such as rotationally and axially movable and/or only axially movable. Movement of the rigid force transfer body relative to the housing in the distal direction may be prevented or constrained by way of the connection features.

In an embodiment, the cartridge bias system has a housing contact area, where the cartridge bias system contacts the housing. The cartridge bias system may abut the housing in the housing contact area. The housing contact area, is expediently formed by the resilient member, preferably a metal spring member. The housing contact area may react the force transferred through the cartridge bias system.

In an embodiment, the cartridge bias system has a cartridge contact area. The cartridge bias system expediently contacts the cartridge in the cartridge contact area. Particularly, the cartridge bias system may abut the proximal end of the cartridge in the cartridge contact area. The cartridge contact area may be formed by the rigid force transfer body or by a resilient member of the bias system, such as one which is integrated with the rigid force transfer body in the unitary body structure or a separate resilient member which may be secured to the rigid force transfer body. Accordingly, an area of a distal surface of the rigid force transfer body or a resilient member may serve as cartridge contact area. The cartridge contact area and the housing contact area expediently face in opposite axial directions. The housing contact area may face in the proximal direction and the cartridge contact area may face in the distal direction.

In an embodiment, the second load transfer surface and the first load transfer surface and/or the housing contact area and the cartridge contact area are radially and/or axially offset.

In an embodiment, the radial distance between the cartridge contact area and the housing contact area and/or between the first and second load transfer surfaces is greater than or equal to one of the following values: 0.5 mm, 0.75 mm, 1.0 mm, 1.25 mm, 1.3 mm, 1.35 mm, 1.375 mm.

In an embodiment, the radial distance between the cartridge contact area and the housing contact area and/or between the first and second load transfer surfaces is less than or equal to one of the following values: 4 mm, 3 mm, 2.5 mm, 2.0 mm, 1.75 mm, 1.5 mm, 1.4 mm. 1.375 mm. Ranges may be formed by combining arbitrary upper limits of the previous sentence with arbitrary lower limits of the previous paragraph. Thus, for example, the radial distance may be between 0.5 mm and 4 mm.

In an embodiment, the radial distance between the cartridge contact area and the housing contact area and/or between the first and second load transfer surfaces is determined by the difference in diameters, particularly in outer diameters, between a standard 3.0 mL cartridge and a standard 1.5 mL cartridge. Specifically, the distance may be half the difference in diameters accounting for a symmetrical arrangement with respect to a main axis of the device or cartridge. This difference in the diameters between 3.0 mL cartridges and 1.5 mL cartridges is approximately 2.75 mm (11.4 mm-8.65 mm), where 2.75 mm/2=1.375 mm.

In an embodiment, the axial distance between the cartridge contact area and the housing contact area and/or between the first and second load transfer surfaces is greater than or equal to one of the following values: 1 mm, 2 mm, 3 mm, 4 mm, 5 mm, 6 mm. Alternatively or additionally, the axial distance between the cartridge contact area and the housing contact area may be less than or equal to 10 mm, 8 mm, 7 mm, 6 mm. Ranges may be formed by combining arbitrary upper and lower limits of the previous two sentences.

In an embodiment, the total length of the rigid force transfer body in the axial direction is expediently greater than or equal to the difference in lengths between a 3.0 mL cartridge and a 1.5 mL cartridge and/or one of the values stated above.

Thus, the axial extension of the rigid force transfer body may be greater than or equal to the difference of the length of a 3.0 mL cartridge and the length of a 1.5 mL cartridge. The length difference between these cartridges is approximately 6 mm. Accordingly, differences in the ranges defined by the values above are suitable to adjust a drug delivery device with a cartridge bias system by way of a rigid force transfer body to a different cartridge such as from a 3.0 mL cartridge to a 1.5 mL cartridge reusing the entire remaining bias system. As the axial offset between the load transfer surfaces is the relevant value for the design of the length of rigid force transfer body, the actual length may be greater than the length difference between two cartridges.

Standard 3.0 mL cartridges have a diameter of 11.4 mm and a length of 64 mm and standard 1.5 mL cartridges have a diameter of 8.65 mm and a length of 57.8 or about 58 mm.

If the radial and axial distances between the load transfer surfaces of the rigid force transfer body are chosen according to the differences in length and/or diameter, e.g. outer diameter, between two different cartridges, using one drive mechanism in conjunction with cartridges of different dimensions is facilitated without the need to redesign the resilient member(s) used in the cartridge bias system of the existing drive mechanism. The rigid force transfer body may be used as a spacer to account for the difference in length and diameter and be applied if required for the particular cartridge. Alternatively, one resilient member of the system or all resilient members of the existing bias system could be redesigned for the cartridge of the different dimension and the remaining mechanism or a majority of the components thereof may be unchanged.

In an embodiment, the rigid force transfer body is a sleeve. The piston rod of the drive mechanism may be arranged to travel through the sleeve. The piston rod may extend or move through the entire cartridge bias system.

In an embodiment, the housing comprises a piston rod guide section. The piston rod guide section may be provided with a piston rod guide feature which is arranged to cooperate with the piston rod to guide movement of the piston rod relative to the housing. The piston rod guide section may be radially offset from an inner surface of the housing. The cartridge bias system or one or more elements thereof, e.g. the rigid force transfer body or at least a section thereof, one resilient member or two resilient members, may be arranged between the inner surface of the housing and an outer surface of the piston rod guide section. A hollow may be formed between the outer surface of the piston rod guide section and the inner surface of the housing. In this way, the rigid force transfer body and/or the cartridge bias system may be provided in a region of the device without additional or significant additional space consumption. Accordingly, the room between the piston rod guide section and the inner wall of the housing which may be provided anyway, for example to retain existing resilient members in a drug delivery device, may be used to accommodate the rigid force transfer body to adjust the existing drug delivery device to a cartridge with a reduced length and/or diameter, for example.

In an embodiment, the cartridge is arranged in a cartridge holder. The cartridge holder may be connected to the housing, e.g. to a distal end thereof. Via the cartridge holder, the cartridge may be secured relative to the housing. The cartridge may be, preferably permanently, secured in the cartridge holder. That is to say, a cartridge assembly may be provided which comprises the cartridge and the cartridge holder, where the cartridge is secured in the cartridge holder. The cartridge assembly may be provided as a single disposable item. The cartridge assembly may be a consumable item for the drug delivery device. The item may be sold separately, e.g. in a pharmacy. Thus, as it is always arranged within a cartridge holder, the cartridge is properly protected by the cartridge holder at any time after being sold in the pharmacy and does not have to be introduced into the cartridge holder by a user.

In an embodiment, a proximal end of the cartridge body is distally offset from a proximal end of the cartridge holder. A section of the cartridge bias system, e.g. the rigid force transfer body or the unitary body structure or a section thereof, may be arranged within the cartridge holder. The cartridge bias system may extend from outside of the cartridge holder into the cartridge holder when the cartridge holder is connected to the housing. At least one resilient member of the cartridge bias system is preferably arranged outside of the cartridge holder.

In an embodiment, the cartridge holder is releasably connected to the housing. Accordingly, if the last dose of drug or medicament from the cartridge has been dispensed and the cartridge has been emptied, the cartridge may be replaced and the drive mechanism of the drug delivery device may be reused in conjunction with a different cartridge. Thus, the drug delivery device may be a reusable drug delivery device.

Another aspect relates to an arrangement comprising two drug delivery devices, a first drug delivery device and a second drug delivery device. The first drug delivery device is a drug delivery device as disclosed above, where the cartridge is a first cartridge, the drive mechanism is a first drive mechanism and the cartridge bias system is a first cartridge bias system. Consequently, the first cartridge bias system comprises the rigid force transfer body. The second drug delivery device comprises a second cartridge, a second cartridge bias system and a second drive mechanism. The second cartridge bias system may not have a rigid force transfer body. Specifically, aside from the rigid force transfer body, the second cartridge bias system may be formed in accordance with the first cartridge bias system. The second drug delivery device may also comprise a second drive mechanism. The first cartridge and the second cartridge may have different lengths and/or diameters. The rigid force transfer body of the first cartridge bias system expediently compensates or is suitable to compensate the differences in length and/or diameter between the first cartridge and the second cartridge. The second cartridge may have greater length and/or diameter than the first cartridge.

The first cartridge and the second cartridge may contain the same drug or medicaments or different drugs or medicaments, or the same drug or medicament formulation or different drug formulations or medicament formulations. The first cartridge and the second cartridge may contain different volumes of liquid. In the present context "different drugs" may mean that the cartridge units contain drugs based on different active pharmaceutical ingredients. "Different drug formulations" may mean that the formulations may be based on the same active pharmaceutical ingredient but the cartridges comprise liquid with different concentrations of the active pharmaceutical ingredient, for example.

The first device and the second device may have equal inner and/or outer diameters of the housing and/or the cartridge holder, specifically equal maximum inner and/or maximum outer diameters of the housing and/or the cartridge holder. Specifically the outer dimensions and the outer appearance of the two devices may be the same although the volume of liquid contained in the cartridges and/or the dimensions of the cartridges may be different.

Still further, the drive and/or dose setting mechanisms of the drug delivery devices may operate alike. Thus, a user may be familiar with one device already and can use the other device without any negative feelings which he might likely have if he were to adjust to a new device which has a new outer shape and a new way of operation.

Yet another aspect relates to a method of modifying a drug delivery device for the use with a different cartridge. This may result in a drug delivery device as discussed above. The drug delivery device to be modified comprises a housing, a drive mechanism, where the drive mechanism is retained in the housing. The drug delivery device comprises a second cartridge containing a drug or a medicament and a cartridge bias system which is configured to exert a force onto the second cartridge. This device may be modified for the use with a first cartridge. The first cartridge may have a smaller diameter and/or length as compared to the second cartridge. The method may comprise the following steps: At first, the difference in length and/or diameter between the first and second cartridges is determined. Thereafter, a rigid force transfer body may be provided, e.g. produced, such as by injection molding. The force transfer body is expediently dimensioned to compensate the difference in length and/or diameter between the first and second cartridges which has been determined previously. Expediently, the rigid force transfer body is also dimensioned to fit in the housing of the device which should be modified. Thereafter, the rigid force transfer body may be integrated into the cartridge bias system to provide a modified drug delivery device. Integrating the rigid force transfer body into the cartridge bias system may comprise mounting the rigid force transfer body into the housing and/or operatively connecting the rigid force transfer body with one or more resilient members of the cartridge bias system of the drug delivery device which is to be modified. After the rigid force transfer body has been integrated into the cartridge bias system, a cartridge bias system is provided which can interact with the first cartridge where the resilient member(s) of the existing bias system can be reused. Alternatively, one or more resilient members may be provided in addition to the force transfer body to substitute one or more resilient members of the existing cartridge bias system.

Thus, by way of providing the rigid force transfer body within the cartridge bias system, differences in the dimensions between two cartridges can be accounted for and a drive mechanism and/or dose setting mechanism can be used in conjunction with a different cartridge without significant or major adjustments in the parts or working principle of the dose setting and/or drive mechanism. Especially, resilient members for the cartridge biasing system may not have to be redesigned, as the entire dimensional adjustment is achieved by the force transfer body.

In a particularly advantageous embodiment, a drug delivery device comprises:

a housing;

a drive mechanism;

a cartridge containing a drug or medicament, the cartridge being retained in a defined position relative to the housing, wherein the drive mechanism is configured to dispense drug from the cartridge;

a cartridge bias system, which comprises at least one resilient member and at least one rigid force transfer body, wherein the rigid force transfer body is movably retained in the housing, wherein the cartridge bias system is arranged and configured to exert a force on the cartridge to maintain the cartridge in the defined position, wherein the force is provided by the at least one resilient member, and wherein the rigid force transfer body is operatively connected to the at least one resilient member such that the force is reacted by the rigid force transfer body.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge holder, or the drug delivery device. "Proximal" may refer to a direction away from the distal or dispensing end or an end which is or is to be arranged further away from the distal or dispensing end of the cartridge, the cartridge holder, or the drug delivery device.

The terms "axial", "radial", and "angular" or "azimuthal" to the extent as used herein may be used with respect to a main longitudinal axis of the device, the cartridge, the housing or the cartridge holder, e.g. the axis which extends through the proximal and distal ends of the cartridge, the cartridge holder, the housing or the drug delivery device.

Features disclosed above in conjunction with different aspect or embodiments should not be regarded as only referring to the recited aspect or embodiment. Rather, the features also apply for the other embodiments or aspects. For example, features disclosed in conjunction with the device do also apply for the arrangement and/or the method and vice versa. Of course, features disclosed in specific embodiments, be it above or further below, can also be applied in combination with one another and/or with other features of other embodiments or aspects.

BRIEF DESCRIPTION OF THE FIGURES

Further features, advantages and advantageous embodiments of the present disclosure will become apparent from the following description of the exemplary embodiments in conjunction with the drawings.

FIG. 5 illustrates a perspective view of a housing part or housing of the device.

FIG. 6 illustrates a sectional view of the housing or housing part.

FIGS. 7A and 7B illustrate an assembling process, where a rigid force transfer body is assembled to a housing part or housing, where FIG. 7A shows the unassembled state and FIG. 7B shows the assembled state.

FIGS. 15A and 15B show a body structure on the basis of a perspective view, in a deformed state in FIG. 15B and an undeformed state in FIG. 15A.

FIG. 16 shows a schematic sectional view through an embodiment of a drug delivery device.

Like elements, elements of the same kind and identically acting elements may be provided with the same reference numerals in the drawings.

DETAILED DESCRIPTION

Figure 1:
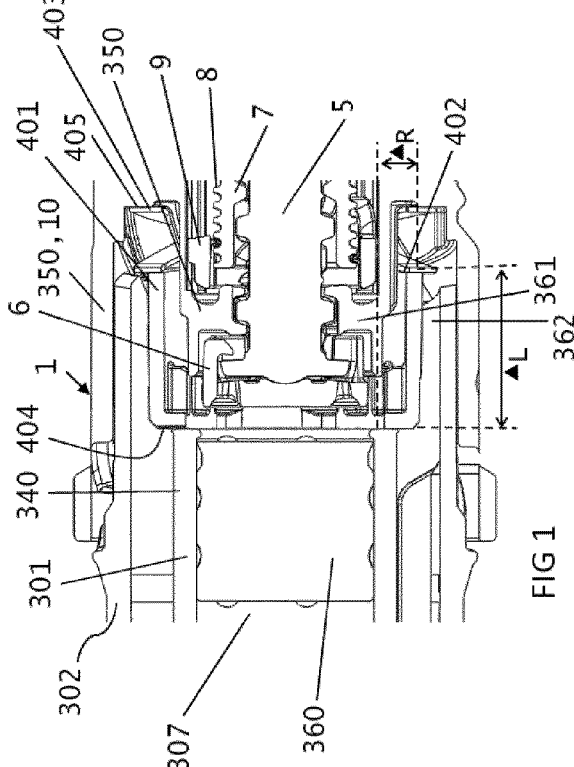
FIG. 1 shows a schematic sectional view of a section or region of an embodiment of a drug delivery device.

In the following, in conjunction with FIGS. 1 through 7B, an embodiment of a drug delivery device and, in particular, an embodiment of a cartridge bias system or arrangement is described. As is apparent from the region of the drug delivery device 1 which is shown in FIG. 1, the drug delivery device 1 comprises a cartridge 301, a cartridge holder 302, and a housing part 350. The cartridge 301 is retained and arranged in the cartridge holder 302. The entire cartridge 301 may be arranged within the cartridge holder 302. The length of the interior of the cartridge holder may be greater than the length of the cartridge. The cartridge 301 may be permanently secured to the cartridge holder 302 such that the cartridge assembly which comprises cartridge 301 and cartridge holder 302 may form a consumable item. The consumable item may be sold in a pharmacy. The cartridge holder 302 is, preferably releasably, connected to the housing part 350, for example via a threaded or bayonet-type connection. The housing part 350 may be an outer housing of the drug delivery device or an additional part which is, preferably axially and rotationally, locked to a housing 10 of the drug delivery device, preferably the outer housing. The housing 10 retains components of a dose setting and/or drive mechanism of the drug delivery device 1. The cartridge 301 holds a drug or medicament 307, preferably a liquid drug formulation. At the proximal end, that is to say that end of the cartridge 301 opposite of the distal end via which the drug 307 can be dispensed from the cartridge, the interior of the cartridge 301 is closed by a movable bung or stopper 360. The bung expediently seals the cartridge proximally. Provided that fluid communication between the interior of the cartridge and the exterior is provided, e.g. by a needle piercing a septum of the cartridge at the distal end (not illustrated), movement of the bung 360 in the distal direction relative to a cartridge body 340 to dispense drug 307 from the cartridge. The drug delivery device 1 is preferably a variable dose device, where the dose of drug which is to be dispensed from the device can be set by the user and is not predefined by the design of the device such as is the case in a fixed dose device. The proximal direction is the direction to the right in FIG. 1 and the distal direction is the one to the left.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, TT-401, BHM- 034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F(ab') 2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The drive mechanism which is retained in the housing 10 or the housing part 350 comprises a piston rod 5, for example a lead screw. Other types of piston rods could be used as well, e.g. toothed rod, or the like. The piston rod 5 may be arranged to drive the bung 360 distally relative to the cartridge body 340. The piston rod 5 may rotate relative to the housing during drug delivery. Consequently, as its interface with the bung 360, the piston rod 5 may be provided with a bearing 6, where the piston rod 5 is rotatable relative to the bearing 6 which, may be axially connected or locked to the piston rod 5. Thus, when the bearing 6 contacts the bung 360, rotational movement of the piston rod 5 relative to the bung may still be possible without having to account for the friction between piston rod and bung. Of course, alternatively, a piston rod of a different design may also be provided. For example, the piston rod may be only moved axially during dose delivery.

The drive mechanism may furthermore comprise a mechanism which transfers a user exerted force from a button or actuator of the device (not illustrated), which forms the user interface, to the piston rod 5. The drive mechanism may furthermore comprise a drive member or drive sleeve 7. The drive member 7 may be rotatable and/or axially displaceable relative to the piston rod 5 in the proximal direction during dose setting and/or transfer the force to the piston rod which is required to generate a distal movement of the piston rod during dose delivery. The drive member 7 may be coupled to a last dose nut 9. An outer surface of the drive member 7 may be provided with a thread 8, which may be engaged to the last dose nut 9. The last dose nut may act as a follower to track how much drug has already been dispensed from the device and, when a final position is reached relative to the drive member, prevent that a dose is set which exceeds the quantity of drug 305 still remaining in the cartridge 301. Thus, the last dose nut may be displaced relative to the drive member during dose setting but stay in position relative to the drive member during dose delivery. This results in a displacement of the last dose nut towards an end position relative to the drive member while the cartridge is emptied. In the end position, increasing the dose may be blocked. This indicates that the cartridge is empty. Thus, when the available drug has been dispensed, the cartridge holder may be detached from the housing and a new cartridge assembly or cartridge may be connected to the housing.

The piston rod 5 is, e.g. threadedly, engaged with or guided by a piston rod guide section 361 of the housing part 350 or the housing 10. The piston rod 5 may be threadedly engaged with the housing 10, 350 via one or more thread features provided on an interior surface of the piston rod guide section 361. Accordingly, relative rotation between the piston rod and the housing results in an axial displacement of the piston rod. Thus, the drive member may transfer a force to the piston rod, which causes the piston rod to rotate relative to the housing during dose delivery.

Between the piston rod guide section 361 and an inner surface of the housing, a hollow or space 362 may be formed. The hollow 362 may provide a region, where components of a cartridge bias system can be arranged without interfering significantly with the drive mechanism.

An embodiment of the cartridge bias system 400 is described in the following. The cartridge bias system 400 comprises a rigid force transfer body 401, e.g. from a plastic material. The cartridge bias system 400 further comprises at least one, expediently separate, resilient member 402 in addition to the rigid force transfer body. The resilient member 402 may be a spring member such as a metal spring member. For example the resilient member 402 is a spring washer. The rigid force transfer body 401 may be arranged between the at least one resilient member and the cartridge. In the embodiment discussed in conjunction with FIGS. 1 through 7B, the cartridge bias system comprises a second separate resilient member 403. The second resilient member may be a spring member such as a metal spring member, e.g. a spring washer. The spring washers 402, 403 may be arranged such that concavely shaped portions of the washer-like surfaces of the spring washers face one another to maximize axial deformability and/or the force transferable by the cartridge bias system.

Figure 2:
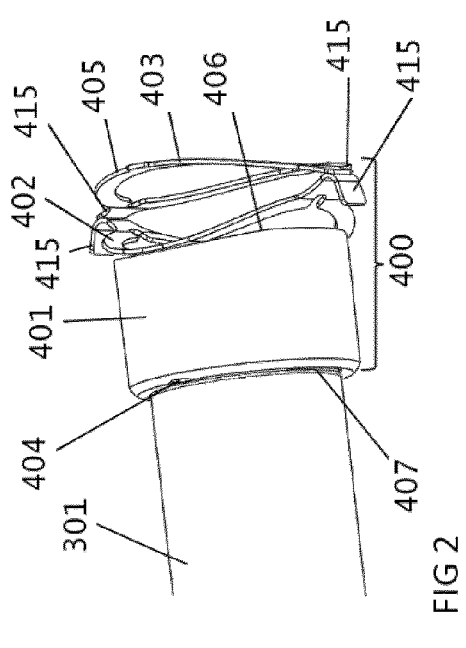
FIG. 2 shows on the basis of a schematic perspective view an embodiment of a cartridge bias system employed in the device.
Figure 10:
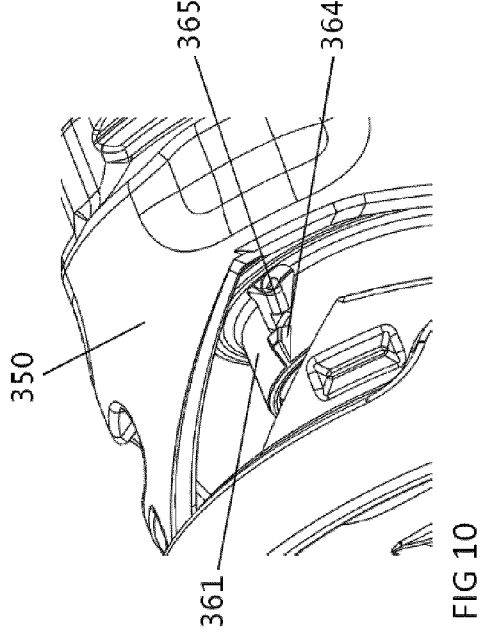
FIGS. 10 and 11 show different perspective views of the housing part of FIG. 8.
Figure 11:
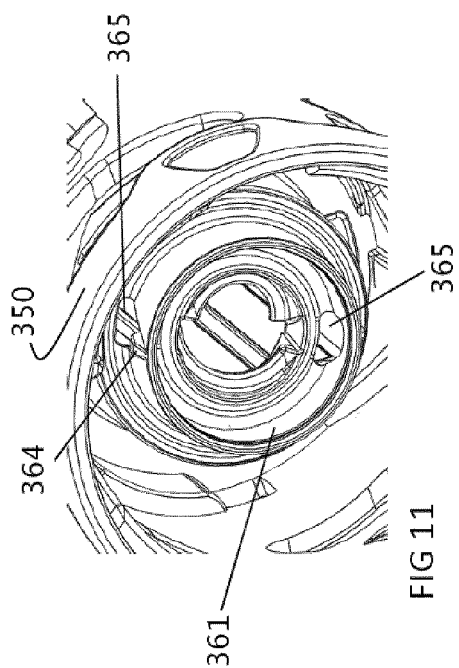
Figure 8:
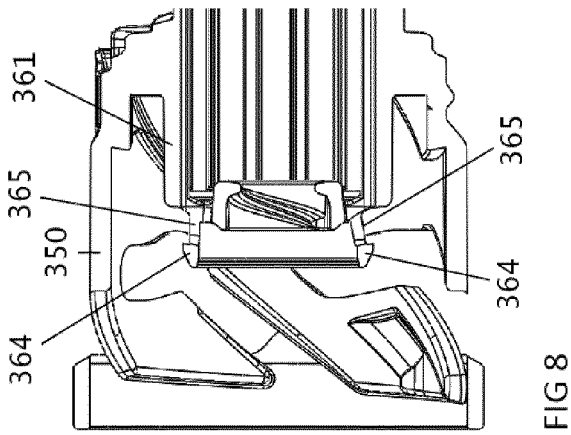
FIG. 8 shows a schematic sectional view through an embodiment of a housing part.
Figure 9:
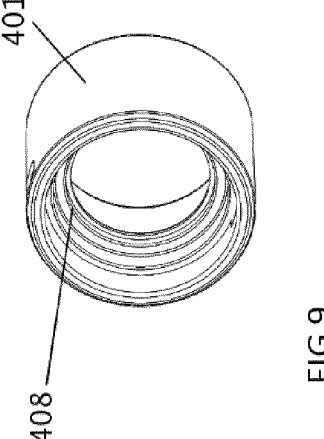
FIG. 9 shows a perspective view of an embodiment of the rigid force transfer body.

In the embodiment depicted in FIGS. 1 and 2, the first and the second resilient member 402, 403 are arranged proximally with respect to the rigid force transfer body 401. The force transfer body 401 is, therefore, arranged between the first resilient member and the cartridge and also between the second resilient member and the cartridge. By means of the axially rigid force transfer body, an axially directed force can be transferred from the resilient members to the cartridge in order to bias the cartridge 301 into the distal direction in a defined position relative to the cartridge holder. This enables to maintain the cartridge in the defined relative position and increases dose accuracy.

The cartridge bias system 400 has a cartridge contact area 404. The cartridge contact area is formed by a distal surface area that is to say a surface facing in the distal direction of the cartridge bias system. The cartridge bias system 400 furthermore has a housing contact area 405, where the cartridge bias system contacts the housing. The housing contact area 405 may be formed by a proximally facing surface of the cartridge bias system. The contact areas 404, 405 enable that the cartridge bias system may be mechanically contacted by the cartridge, e.g. by a proximal rim of the cartridge body, and the resilient member or the resilient members may be elastically biased by axially displacing the cartridge relative to the housing during attachment of the cartridge such as by attaching the cartridge holder 302 to the housing part 350 or the housing 10. In the depicted embodiment in FIGS. 1 and 2, the cartridge contact area 404 is formed by the rigid force transfer body 401 and the housing contact area 405 is formed by one of the resilient members 402, 403, e.g. the more proximal one if two resilient members are present or by the resilient member, if only one is present, which is also possible. The rigid force transfer body 400 may be, entirely or only partly, received in the cartridge holder 302. Accordingly, the outer diameter of the rigid force transfer body may be less than the inner diameter of the cartridge holder 302. The opening of the resilient members may have equal inner diameters. The opening of the respective resilient member may have a diameter greater than the outer diameter of the cartridge at the proximal end.

The rigid force transfer body is axially movable relative to the housing, where the resilient member(s) is (are) elastically deformed when it is moved proximally and may relax, when the body moves distally, e.g. when the cartridge is changed. The axial movement of the rigid force transfer body relative to the housing may be constrained, especially in the distal direction and/or in the proximal direction. In the distal direction, this may be done by a stop surface provided on the housing or housing part which prevents the rigid force transfer body from falling out of the housing or housing part when the cartridge holder 302 is disconnected.

The first resilient member 402 may mechanically contact the rigid force transfer body 401, the second resilient member 403 may mechanically contact the first resilient member and be arranged to contact the housing in the housing contact area 405. A force created by deformation of the resilient members when the cartridge pushes the force transfer body proximally, where the force acts in the distal direction, is transmitted to the cartridge via the rigid force transfer body and to the housing by means of one of the resilient members. This keeps the resilient member(s) biased when the cartridge is connected to the housing, where the resilient force is reacted by the housing and the cartridge.

The piston rod 5 may extend through and be guided through the resilient member(s) and the rigid force transfer body 401. Thus, the force transfer body and/or the resilient members can be arranged radially outwardly offset from the piston rod. The force transfer body and/or the resilient member(s) are also preferably arranged radial outwardly with respect to the piston rod guide section 361 of the housing part 350. Expediently, they can be arranged in the hollow 362 defined between the piston rod guide section and an inner surface of the housing. In this way, although the rigid force transfer body 401 is provided, no significant additional packaging space may be required.

The rigid force transfer body is preferably not or not significantly compressible under the regular axially directed force which occur when the cartridge is connected to the housing by the cartridge retainer or holder 302.

The cartridge contact area 404 and the housing contact area 405 may be axially and radially offset. The radial offset may correspond to the difference in radius or diameter between a 3.0 mL cartridge and a 1.5 mL cartridge.

A standard 3.0 mL cartridge has an outer diameter of 11.4 mm and a length of 64 mm and a standard 1.5 mL cartridge has an outer diameter of 8.65 mm and a length of 57.8 mm or about 58 mm. Accordingly, the radial offset between cartridge contact area 404 and the housing contact area 405 may be equal to about 1.375 mm.

In case of doubt, the centers of the respective contact area as seen in sectional view perpendicular to the main axis of the device may be taken as origin to determine the distance. Alternatively, a radial inward end of the housing contact area and a radial outward end of the cartridge contact area may be used to determine the distance.

The rigid force transfer body may form a spacer which is used to adjust an existing mechanism for a drug delivery device to a cartridge having a reduced length and/or diameter such as a mechanism which is designed for a 3.0 mL cartridge to be used in conjunction with a 1.5 mL cartridge. The cartridges may contain the same drugs or drug formulations or different drugs or drug formulations. For example, the 1.5 mL cartridge may contain the same drug but in a different concentration, e.g. insulin in a higher concentration than the 3.0 mL drug. Thus, in the depicted embodiment, the cartridge may be a 1.5 mL cartridge. If a 3.0 mL cartridge is employed, the rigid body may be dispensed with or a shorter body may be employed. By means of the dimensions of the rigid force transfer body 401, the difference between the length and the diameter of the 1.5 mL cartridge and 3.0 mL cartridges can be compensated. In FIG. 1, the difference in radius (which is half the diameter) is illustrated by $\Delta_R$ and the difference in length is illustrated by $\Delta_L$. The length of the force transfer body may be determined by the length difference between the 3.0 mL cartridge and the 1.5 mL cartridge or be greater. However, the axial separation between load transfer or interface surfaces of the body, where the body interfaces with another element, e.g. a resilient member on the proximal side and with the cartridge on the distal side, is expediently equal to the length difference even if the body itself has a greater length.

Consequently, apart from the force transfer body, the cartridge bias system can stay the same, especially the springs need not to be re-dimensioned. The inner diameter of the opening in the resilient member(s) may correspond to the one of a 3.0 mL cartridge, such that the respective member could be used to abut a proximal end of the cartridge body of the 3.0 mL cartridge. Thus, components which have proven their function in a 3.0 mL cartridge device can be reused in conjunction with a 1.5 mL cartridge device. The outer appearance of the devices may stay the same regardless of the cartridge retained therein. The inner diameter of the opening in the resilient member(s) may correspond to the one of a 3.0 mL cartridge, such that the respective member could be used to abut proximal end of the 3.0 mL cartridge.

The requirement to provide sufficient biasing force for a range of deformation values, e.g. resulting from variations in manufacturing tolerances, means that a minimum quantity of energy must be stored within the resilient elements of the biasing arrangement or system. This energy storage requirement will be more easily met with large diameter springs rather than small diameter springs due to the larger volume of metal that may be included. The additional diameter available also potentially reduces the axial space requirements of the biasing arrangement. In a typical pen injector, packaging space will be at a premium close to the axis of the device due to the presence of the dispensing or drive mechanism (e.g. bearing, piston rod, piston rod guide section, drive member and/or last dose nut). The use of a spacer or rigid force transfer body to 'step out' to a larger diameter allows the use of metal bias springs which are of larger diameter than the aforementioned components. This allows the cartridge biasing arrangement to wrap around the aforementioned components rather than requiring that an axial gap be introduced between them. This advantage is independent of whether the device is adjusted to a differently shaped or dimensioned cartridge or not.

Figure 4:
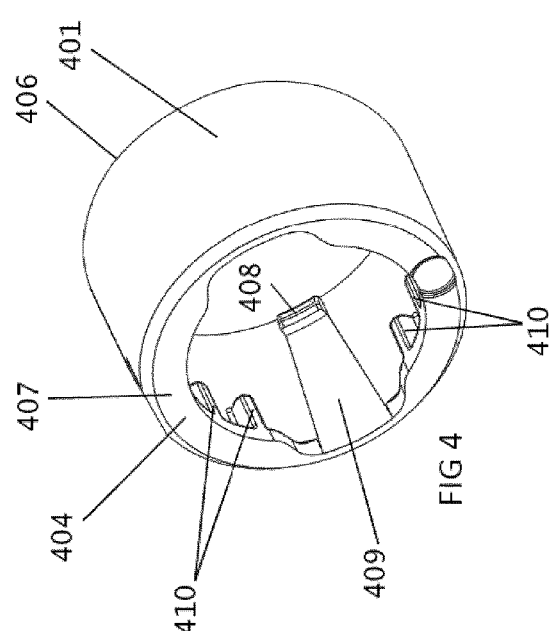
FIG. 4 shows a part of a section of FIG. 1 with highlighted areas.

FIG. 4 illustrates that the cartridge bias system can be constrained to a region outside of the one where elements of the drive mechanism or guiding elements associated with elements of the drive mechanisms are arranged. Specifically, the shaded region "A" is the one where the bias system is arranged and the region "B" is the one where the drive mechanism is arranged. For simplicity, only the upper half of the device 1 is shown in FIG. 4, where the device may be symmetric with respect to the main longitudinal axis X of the device.

Figure 3:
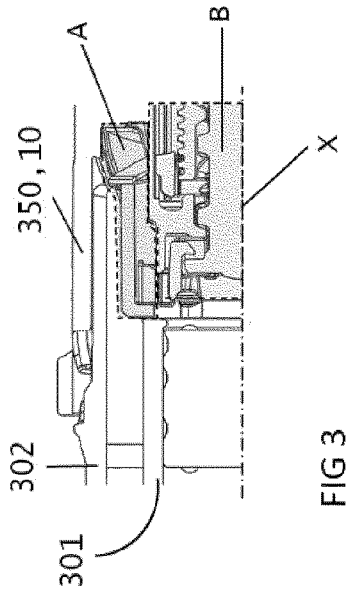
FIG. 3 shows a component of the cartridge bias system, a rigid force transfer body, on the basis of a perspective view.

To compensate for the length difference between different cartridges, the axial distance between load transfer surfaces of the rigid force transfer body should be determined by or equal to the length difference. In the embodiment shown in FIG. 3, the distal load transfer surface 407 of the force transfer body 401 is formed in the area of the cartridge contact area 404. However, as will be shown below, the force transfer body need not immediately abut the cartridge such that the cartridge contact area and the distal load transfer surface do not have to coincide. The proximal load transfer surface 406 may be formed by the proximal end of the force transfer body, which may be that end, which is mechanically abutted by the first resilient member 402. As depicted in FIG. 3, the force transfer body 401 has a sleeve-like shape. A flange at the distal end, which is inwardly directed, may provide the load transfer surface 407 and/or the cartridge bearing area 404.

As already discussed previously, the force transfer body 401 is expediently assembled to the housing or the housing part 350. For this purpose, one or more connection features 408 are provided. In FIG. 3 only one connection feature 408 is shown, although a plurality are preferably provided. For example, at the diametrical opposite position for the depicted connection feature, another connection feature 408 may be provided. Also, more than two connection features 408 may be provided, which are preferably uniformly distributed in the angular or azimuthal direction.

The respective connection feature 408 may be a snap or clip feature. In order to provide for flexibility, in the radial direction, the flange may have a reduced radial extension in an area angularly overlapping with the connection feature 408, but axially separated therefrom. alternatively or additionally the wall thickness of a sidewall of the body 401 may be reduced in an which is angularly aligned with the connection feature in order to increase flexibility. Thus, a recess 409 may extend axially away from the connection feature in the proximal and/or distal direction. In FIG. 3, only a distally extending recess 409 is shown.

The connection feature may extend radially inwardly from the force transfer body into the opening of the body through which the piston rod may extend. The force transfer body furthermore comprises guide or stabilization features 410, e.g. ribs extending in the axial direction. A radially inwardly facing surface of the respective guiding or stabilization feature may bear against the radially outwardly facing surface of the housing part 350, e.g. an outward surface of the piston rod guide section 361 in order to radially stabilize the positon of the force transfer body 401 when assembled. Accordingly, the guide features 410 expediently abut the housing when the cartridge holder with the cartridge has been disconnected from the housing and/or when the cartridge holder has been connected to the housing. Specifically the guide features may cooperate with the housing in any axial position of the force transfer body relative to the housing when the body has been assembled to the housing. By means of the connection feature 408 or a plurality of connection features, the rigid force transfer body 401 may be mounted to the housing e.g. axially constrained and/or rotationally locked.

FIG. 5 shows the housing part 350 where FIG. 6 shows a sectional view through the housing part 350 of FIG. 5. with the piston rod guide section 361 and the hollow 362. As is apparent, the housing part 350 has an opening 363 which extends radially from an outer surface of the housing part towards the interior, e.g. into the hollow 362. The opening 363 may interact with connection or guide features 415 of one or both resilient members 402 and 403. For example, these guide features 415 may be arranged or retained in the opening to axially and/or rotationally constrain the respective resilient member to the housing. As is also apparent from FIG. 6, the housing part 350 is provided with a connection feature 364 or a plurality of connection features 364. The arrangement of the connection features 364 preferably matches the one of the connection features 408 of the force transfer body. In an exemplary embodiment depicted in FIG. 6, the respective connection feature 364 may be a groove. A proximally directed surface which delimits the groove distally may form a distal stop for movement of the force transfer body 401 relative to the housing part 350. As a plurality of separate connection features 364 is provided which are separate from each other, a rotational alignment of the force transfer body 401 relative to the housing part 350 has to be performed such that the angular position of the connection features 408 and 364 match before the force transfer body and the housing part are assembled utilizing relative axial movement. This is depicted in FIG. 7A which shows a situation right before the force transfer body 401 is assembled to the housing part 350 where the arrow denotes the axial movement. FIG. 7B shows the body 401 in a state where it has been assembled. Further components, e.g. the resilient member(s), are not shown for illustration purposes. During the assembling, the connection feature 408 may flex radially outwardly, which is permitted and, once the connection feature 364 has been reached, flex again radially inwardly such that a distally facing surface of the connection feature 408 can abut a proximally facing surface of the housing part 350 which delimits the groove as connection feature 364 distally. Snap features or clip features for the connection between the body 401 and the housing part 350 can be integrated into the body by way of injection molding, preferably by low-cost injection molding such as open-shot injection molding without the use of sophisticated molds, e.g. molds involving shutters or sliders which increase the costs of the molds significantly.

The connection feature 364 may overlap axially and/or azimuthally or angularly with the opening 363. The connection feature 364 may be radially offset with respect to the opening 363. Due to this overlap, a connection feature 364 can be formed by means of a slide of an injection mold used for the housing part 350. As the housing part is sophisticatedly designed anyway and the tooling involves considerable cost already, an additional slide is not so significant cost-wise. The connection features could also be configured in a different way. Such a modification of the embodiment discussed previously is discussed below in conjunction with FIGS. 8 through 12B.

As the force transfer body is, in this embodiment arranged distally relative to all resilient members of the bias system, these members are invisible for the user and/or cannot be tampered with when the cartridge has been removed.

Figure 12A:
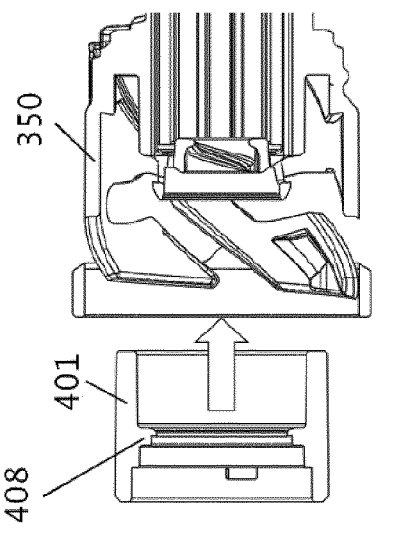
FIG. 12A illustrates the force transfer body before it is mounted to the housing part and FIG. 12B illustrates the situation after the body has been mounted.
Figure 12B:
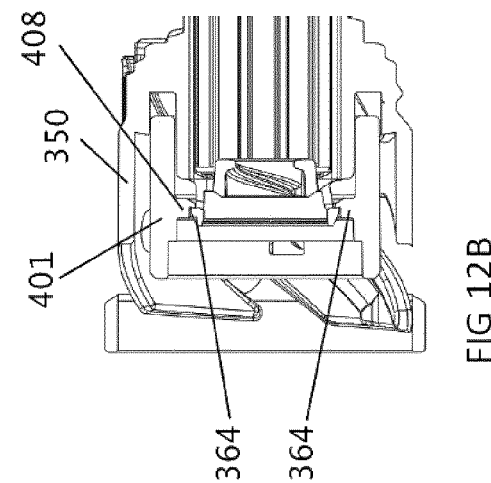

The rigid force transfer body can also be connected differently to the housing. One option is illustrated in conjunction with FIGS. 8 through 12B, where only the differences over the previous embodiment are discussed. Here, the connection features 364 on the housing part 350 are formed by one or more snap features and not by grooves. A proximal surface of the respective connection feature 364 delimits an opening 365 which protrudes radially through an outer wall of the piston rod guide section 361 in the distal direction. Connection features 364 of this kind can be formed by upstands on a core pin of the molding tool used for defining the interior of the piston rod guide section 361. The upstands may radially protrude from the core pin. The force transfer body 401, in this case, has a circumferentially extending flange as connection feature 408. Thus, when assembling the body 401 to the housing part 350, proper rotational alignment of the body 401 an the housing part is irrelevant as compared to the previously described embodiment. Clearly, a distally facing surface of the connection feature 408 is arranged to abut a proximally facing surface of the (respective) connection feature 364 after the assembly has been completed as shown in FIG. 12B. The flexibility required for the attachment may be provided at least partly by the reduced axial thickness of the snap nose of the connection feature 408 which may flex axially during the assembling process. The required force may be exerted via an oblique proximally facing surface of the connection feature 408, which contacts the housing part during the assembling process. Two springs or resilient members can be arranged at the proximal side of the rigid force transfer body or only one spring or resilient member can be used. Generally, features disclosed in conjunction with different embodiments may be combined with one another or substituted with each other as the case may be.

Figure 13:
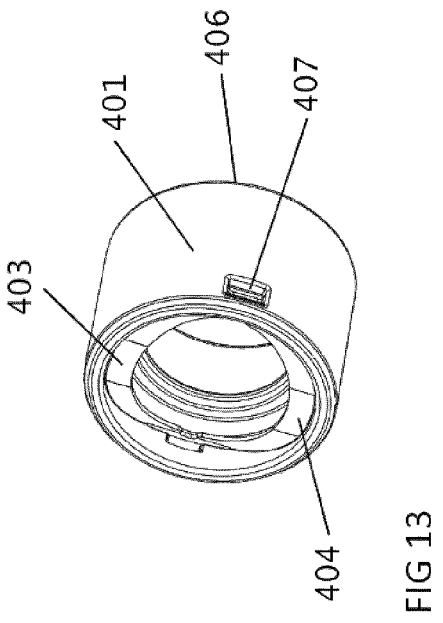
FIG. 13 shows a perspective view of a force transfer body to which one resilient member is assembled.
Figure 14:
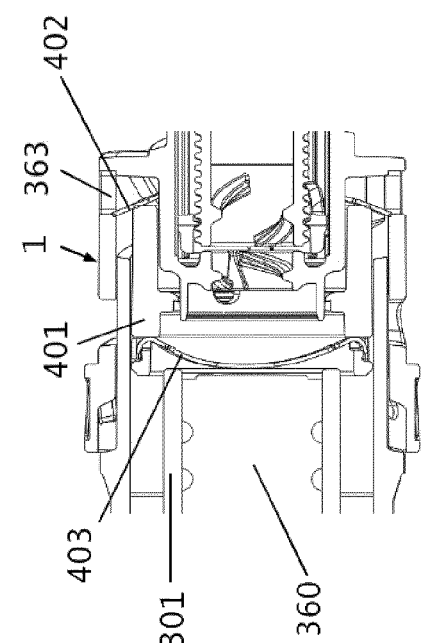
FIG. 14 shows a schematic sectional view of a section or region of an embodiment of a drug delivery device.

Another embodiment of a cartridge bias system is illustrated in FIGS. 13 and 14. In the following, only the differences with respect to the previously disclosed embodiments are discussed. FIG. 13 shows a perspective view of the force transfer body 401. FIG. 14 shows a sectional view through a drug delivery device 1 which corresponds largely to the one discussed in conjunction with FIG. 1. As is apparent from FIG. 13, the cartridge bias system comprises a sub-assembly which comprises or consists of the force transfer body 401 and a spring member as second resilient member 403 which assembled to the body. The diameter of the resilient member 403 may be adjusted to the diameter of the cartridge such that the spring may abut the cartridge at the proximal side as depicted in FIG. 14. The distal load transfer surface 407 of the force transfer body may, in this case, be formed by the distal surface of a mounting feature by which the resilient member 403 is mounted to the force transfer body 401. Thus, a spring member, e.g. a spring washer, can be used to bias the cartridge distally. The resilient member 403 may be clipped into the fore transfer body such that the resilient member 403 may be located in an interior of the force transfer body. Thus, the cartridge contact area 404 may be formed by a distal surface of the resilient member 403 as depicted. The remaining functionality may be as disclosed previously in conjunction with other embodiments.

Locating one of the resilient members on the distal end or distal side of the force transfer body means that the axial travel required for the force transfer body will be reduced. The force transfer body must only travel far enough to create the deformation required for one of the resilient members rather than the sum of the axial deformations required for both resilient members as is the case if both members were arranged on the proximal side as in the FIG. 1 embodiment. This may provide advantages in the design of the connection of the force transfer body to the housing part 350.

Alternatively, as will be discussed in conjunction with the following embodiment, the force transfer body may be integrated into a single unitary body structure together with one resilient member. This embodiment is discussed below in conjunction with FIGS. 15A through 16, where again only differences over the previous embodiments are addressed.

Here a unitary body structure 411, e.g. of plastic, incorporates the rigid force transfer body 401 and also the resilient member 403. The resilient member 403 is arranged at the distal end of the rigid force transfer body 401. Thus, the distal load transfer surface 407 may be formed by the transition region of the body structure 411 between the resilient member 403 and the body 401. The diameter of the resilient member 403 may correspond to the diameter of the cartridge body at the proximal end. The inner diameter of the force transfer body 401 may be greater than the outer diameter of the second resilient member 403. The resilient member may be connected to the force transfer body but have an interspace with respect to the force transfer body to provide resiliency. The resilient member 403 may be formed ring-like with two different web-like connections 412 to the force transfer body 401. At the distal side of the resilient member 403 one or more rigid cartridge contact features 413 may be provided. They may protrude axially from the ring structure of the resilient member 403 and, when the cartridge holder 302 is connected to the housing part 350 abut the proximal end or rim of the cartridge 301.

As depicted in FIG. 16, the resilient member 402, e.g. a metal spring member such as a washer is present as discussed previously. The integration of one of the resilient members into a body structure together with the rigid force transfer body reduces the number of components required and may also simplify the assembly process for assembling the cartridge bias system. In the angular region(s) between the connections 412 one or more flexible regions 414, e.g. arc-like regions, of the resilient member 403 may be formed. The flexible regions may be also designated as flexible arms 414. FIG. 15A shows the flexible arms 414 in a non-flexed state and FIG. 15B shows them in a flexed state, where, for example the proximally facing surface of the flexible arms may contact a distal surface of the force transfer body. When the cartridge holder has been connected to the housing the flexible arms may have been deformed as depicted in FIG. 15B as may have the resilient member 402.

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
5 piston rod
6 bearing
7 drive sleeve
8 thread
9 last dose nut
10 housing
301 cartridge
302 cartridge holder
307 drug/medicament
340 cartridge body
350 housing part
360 bung
361 piston rod guide section
362 hollow
363 opening
364 connection feature
365 opening
400 cartridge bias system 401 rigid force transfer body
402 first resilient member
403 second resilient member
404 cartridge contact area
405 housing contact area
406 load transfer surface
407 load transfer surface
408 connection feature
409 recess
410 guide feature
411 body structure
412 connection
413 cartridge contact feature
414 flexible arm
415 connection/guide feature
A region
B region
X axis

The invention claimed is:

1. A drug delivery device, comprising:
a housing;
a drive mechanism;
a cartridge containing a drug, the cartridge being retained in a defined position relative to the housing, wherein the drive mechanism is configured to dispense the drug from the cartridge; and
a cartridge bias system, which comprises at least one resilient member and at least one rigid force transfer body,
wherein the cartridge bias system is arranged and configured to exert a force on the cartridge to maintain the cartridge in the defined position, wherein the force is provided by the at least one resilient member, wherein the at least one rigid force transfer body is operatively connected to the at least one resilient member such that the force is reacted by the at least one rigid force transfer body, wherein the cartridge is arranged in a cartridge holder which is connected to the housing, and wherein the cartridge bias system extends into the cartridge holder, and wherein the at least one rigid force transfer body is movable within the housing and is configured to be located at a position within the housing according to a length of the cartridge, and
wherein a piston rod of the drive mechanism is arranged to travel through the at least one rigid force transfer body, wherein the housing comprises a piston rod guide section which is provided with a piston rod guide feature which cooperates with the piston rod to guide movement of the piston rod relative to the housing, wherein the piston rod guide section is radially offset from an inner surface of the housing, wherein at least a section of the at least one rigid force transfer body is arranged between an outer surface of the piston rod guide section and the inner surface of the housing, and wherein at least an inner surface of the at least the section of the at least one rigid force transfer body faces towards the outer surface of the piston rod guide section.

2. The drug delivery device of claim 1, wherein the at least one resilient member has a central opening, wherein an inner diameter of the central opening is greater than an outer diameter of the cartridge.

3. The drug delivery device of claim 1, wherein the at least one resilient member of the cartridge bias system comprises two resilient members.

4. The drug delivery device of claim 3, wherein the at least one rigid force transfer body is arranged in a load path between the two resilient members.

5. The drug delivery device of claim 3, wherein the at least one rigid force transfer body is arranged in a load path between the two resilient members and the cartridge.

6. The drug delivery device of claim 3, wherein one of the two resilient members is formed in a unitary body structure with the at least one rigid force transfer body.

7. The drug delivery device of claim 3, wherein one of the two resilient members is rigidly secured to the at least one rigid force transfer body.

8. The drug delivery device of claim 1, wherein the cartridge bias system has a housing contact area where the cartridge bias system contacts the housing and a cartridge contact area where the cartridge bias system contacts the cartridge, wherein the housing contact area and the cartridge contact area are radially and axially offset.

9. The drug delivery device of claim 8, wherein a distal surface of the at least one rigid force transfer body comprises the cartridge contact area.

10. The drug delivery device of claim 8, wherein a distal surface of the at least one resilient member comprises the cartridge contact area.

11. The drug delivery device of claim 8, wherein a radial distance between the cartridge contact area and the housing contact area is greater than or equal to 0.5 mm and less than or equal to 3.0 mm.

12. The drug delivery device of claim 8, wherein a radial distance between the cartridge contact area and the housing contact area is determined by a difference of a diameter of a 3.0 mL cartridge and a diameter of a 1.5 mL cartridge, and wherein an axial extension of the at least one rigid force transfer body is greater than or equal to a difference of a length of the 3.0 mL cartridge and a length of the 1.5 mL cartridge.

13. The drug delivery device of claim 1, wherein the drug in the cartridge is a medicament.

14. The drug delivery device of claim 1, wherein the outer surface of the piston rod guide section faces towards the inner surface of the housing.

15. The drug delivery device of claim 1, wherein the at least the inner surface of the at least the section of the at least one rigid force transfer body is radially separated from the outer surface of the piston rod guide section.

16. An arrangement comprising:
a first drug delivery device comprising:
a housing,
a first drive mechanism,
a first cartridge containing a drug, the first cartridge being retained in a defined position relative to the housing, wherein the first drive mechanism is configured to dispense the drug from the first cartridge, and
a first cartridge bias system, which comprises at least one resilient member and at least one rigid force transfer body,
wherein the first cartridge bias system is arranged and configured to exert a force on the first cartridge to maintain the first cartridge in the defined position, wherein the force is provided by the at least one resilient member, wherein the at least one rigid force transfer body is operatively connected to the at least one resilient member such that the force is reacted by the at least one rigid force transfer body, wherein the first cartridge is arranged in a first cartridge holder which is connected to the housing, wherein the first cartridge bias system extends into the first cartridge holder, and wherein the at least one rigid force transfer body is movable within the housing and is configured to be located at a position within the housing according to a length of the first cartridge, and
wherein a piston rod of the first drive mechanism is arranged to travel through the at least one rigid force transfer body, wherein the housing comprises a piston rod guide section which is provided with a piston rod guide feature which cooperates with the piston rod to guide movement of the piston rod relative to the housing, wherein the piston rod guide section is radially offset from an inner surface of the housing, wherein at least a section of the at least one rigid force transfer body is arranged between an outer surface of the piston rod guide section and the inner surface of the housing, and wherein at least an inner surface of the at least one the section of the at least one rigid force transfer body faces towards the outer surface of the piston rod guide section; and
a second drug delivery device comprising a second cartridge, a second cartridge bias system, and a second drive mechanism,
wherein the first cartridge and the second cartridge have different lengths and/or diameters, wherein the at least one rigid force transfer body of the first cartridge bias system compensates or is suitable to compensate differences in the different lengths and/or diameters of the first cartridge and the second cartridge.

* * * * *